US 6,562,316 B1

(12) United States Patent
Edwards et al.

(10) Patent No.: US 6,562,316 B1
(45) Date of Patent: May 13, 2003

(54) DRUG DELIVERY SYSTEM WITH TWO-STEP TARGETING

(76) Inventors: Katarina Edwards, Biörkgatan 5 K, SE-753 28, Uppsala (SE); Jörgen Carlsson, Karlsrogatan 50, SE-752 39, Uppsala (SE); Stefan Sjöberg, Sibyllegatan 7, SE-752 31, Uppsala (SE)

(*) Notice: Subject to any disclaimer, the term of this patent is extended or adjusted under 35 U.S.C. 154(b) by 0 days.

(21) Appl. No.: 09/555,329
(22) PCT Filed: Dec. 4, 1998
(86) PCT No.: PCT/SE98/02231
§ 371 (c)(1), (2), (4) Date: Sep. 1, 2000
(87) PCT Pub. No.: WO99/29302
PCT Pub. Date: Jun. 17, 1999

(30) Foreign Application Priority Data

Dec. 5, 1997 (SE) .............................. 9704549

(51) Int. Cl.[7] ...................... A61K 51/00; A61K 9/127; A61K 31/70; A61M 36/14
(52) U.S. Cl. .................. 424/1.21; 424/450; 424/178.1; 514/44
(58) Field of Search ............. 424/178.1, 181, 424/450, 1.21; 514/44, 75–78

(56) References Cited

U.S. PATENT DOCUMENTS

| | | | |
|---|---|---|---|
| 5,328,678 A | * 7/1994 | Fujii et al. | |
| 5,599,796 A | * 2/1997 | Schinazi et al. | |
| 5,620,689 A | * 4/1997 | Allen et al. | |
| 5,630,786 A | * 5/1997 | Griffin et al. | |
| 5,643,599 A | * 7/1997 | Lee et al. | 424/450 |
| 5,674,977 A | * 10/1997 | Gariepy | |
| 5,750,390 A | * 5/1998 | Thompson et al. | |
| 5,888,473 A | * 3/1999 | Hawthorne et al. | |
| 5,939,277 A | * 8/1999 | Rakowicz-Szulczynska | 435/7.23 |
| 6,180,766 B1 | * 1/2001 | Schinazi et al. | |

FOREIGN PATENT DOCUMENTS

| WO | wo9614877 | * 5/1996 |
|---|---|---|
| WO | wo9741834 | * 11/1997 |

OTHER PUBLICATIONS

Gedda et al., Intl. J. of Oncology 11(4) : 789–795 (Apr. 1997)—Abstract Only.*
Gedda et al., Two–step Targeting in Advances in neutron capture therapy vol. 11, pp. 382–385, Editors: Larsson et al. Elsevier Science Publishing Amsterdam, The Netherlands (Dec. 1, 1997)—Citation only.*
Sjoberg, Elsevior Science B.V., II:3–21 (1997).*
Mehta et al., Pharmaceuitical Research, 13(3):344–351 (1996).*
Feaks et al.(Synthesis and liposomal delivery to murine tumors, Proc. Natl. Acad. Sci, vol. 91, p. 3029–3033, 1994).*
Gedda et al., Intl. J. of Oncology 11(4) : 789–795 (Oct. 97).*
Gedda et al, "Two–Step Targeting: EGF–Conjugate for Delivery of DNA–Binding Boron Compounds," *Advances in Neutron Capture Therapy, vol. 2, Chemistry & Biology*, Larsson et al, editors, Elsevier Science BV, pp. 382–385 (1997).
Mehta et al, *Pharmaceutical Research*, 13(3):344–351 (1996).
Ghaneolhosseini et al, *Tetrahedron*, 53(51):17519–17526 (1997).
Carlsson et al, *Int. J. Radiation Oncology Biol. Phys.*, 30(1):105–115 (1994).
Kirpotin et al, *Biochemistry*, 36(1):66–75 (1997).
Park et al, *Proc. Natl. Acad. Sci. USA*, 92:1327–1331 (1955).
Lee et al, *J. Biol. Chem.*, 269(5):3198–3204 (1994).
Nilsson et al, *Cancer Research (Suppl.)*, 55:5805a–5810a (1995).
Press, *Tumor Targeting*, 1:31–35 (1995).
Sjöberg, *Elsevier Science B.V.*, II:3–21 (1997).
Westlin et al, *Oncology Reports*, 2:543–548 (undated).
Sjöberg et al, *Journal of Neuro–Oncology*, 33:41–52 (1997).
Gedda et al, *Anti–Cancer Drug Design*, 12:671–685 (1997).

* cited by examiner

*Primary Examiner*—Ethan Whisenant
(74) *Attorney, Agent, or Firm*—Dinsmore & Shohl LLP

(57) ABSTRACT

The present invention relates to a drug delivery system with two-step targeting, which comprises a combination: (a) a lipid carrier provided with cell targeting agent(s) to target the drug delivery system to specific cells or tissues; and (b) a drug enclosed in said lipid carrier and provided with a DNA targeting agent to target the drug to the nuclei of specific target cells. Furthermore, the invention relates to a method of cancer therapy in which the above drug delivery system is administered to a cancer patient. The goal is to treat or analyse both large tumour masses as well as small tumour cell clusters and single spread tumour cells. According to the invention, drug uptake in tumours will be markedly increased at the same time as the interaction of the drug with healthy organs and tissues can be minimized. The invention gives potential to convert palliative into curative treatment.

16 Claims, 1 Drawing Sheet

DRUG DELIVERY SYSTEM WITH TWO-STEP TARGETING

BACKGROUND OF THE INVENTION

In order to increase the efficiency of tumour therapy, the possibilities of using tumour seeking molecules that deliver the toxic agent specifically to the tumour cells are being explored. Radionuclides have recently been applied for cell targeted radiotherapy of malignant lymphomas (Press, 1995) and curative treatments have been achieved in some cases. So far, this is the only known case when therapy, based on macromolecular targeting agents, has been successfully applied. The reasons for the good results are probably a combination of two fortunate circumstances. The lymphoma cells are unusually easy to find for the targeting agent due to the cells main localisation in the systemic circulation. Furthermore, lymphoma cells are among the most radiation sensitive human cells presently known.

In other diseases like melanomas, gliomas and a variety of adenocarcinomas (e.g. prostate, breast and colon tumours) it has not been possible to give curative treatments with targeted radionuclides yet. The limitations appear to be partly due to that the first step in the targeting process (to find the tumour cells) is not efficient enough. A further difficulty is that, when the targeting agent anyhow has succeeded to reach the tumour cells, the energy delivery (the ionisation energy) does not damage the cell enough. The low energy delivery is due to both the limited number of nuclides reaching the cell and the fact that the radioactivity to a large extent is located in the cellular membrane or in the cytoplasm. Such a cellular localisation means that far from all emitted radiation quanta passes through the nuclear DNA. This is very unfortunate since the nuclear DNA is the critical target in the cell and severe damage to DNA is necessary to stop the proliferation of the cell.

Localization in the cell nucleus may be accomplished by linking the nuclides to substances with high affinity for DNA. These nuclide-carrying substances may be DNA-intercalators such as phenantridinium, acridine and naphtalimide derivatives (Sjöberg et al 1997, Ghaneolhosseini et al 1997) or compounds which interact electrostatically with DNA such as spermine, spermidine, and putrecine derivatives (Sjöberg 1997).

Liposomes have for a long time been interesting as potential drug carriers. The unique structure allows transport of both fat soluble and water soluble substances. Furthermore, the endothelium of tumours is more permeable than normal endothelium and a spontaneous accumulation in tumour tissue can be achieved. To increase circulation time and increase the stability of the liposomes it is important to select a proper lipid composition in the liposome membrane. The destabilization of the liposomes can be further minimized when the surface of the liposome is provided with polymers. Several types of polymers give increased circulation time but polyethyleneglycol (PEG) has so far given the best result (Lasic and Martin 1995).

When the liposome, filled with a toxic substance, has reached the target cell the content of the liposome must be emptied. This occurs naturally by passive leakage and the permeability of the liposome membrane can also be modified by varying the composition of the lipids. The uptake by passive diffusion is not very efficient, most of the liposome content is lost already before it reaches the cell membrane. Furthermore, depending on the properties of the drug, such as fat solubility and charge, a substantial part can be trapped in the cell membrane.

A way of increasing the uptake and simultaneously avoid membrane localization, is to utilize ligands, antibodies and antibody fragments or other suitable agents, with high specificity for receptors or other target structures with endocytotoxic ability. Internalization of whole liposomes into cells has been shown in in vitro experiments where folic acid, or a Fab' fragment directed against glycoprotein p185$^{HER2}$ was conjugated to stabilized liposomes (Kirpotin et al. 1997, Lee and Low 1994, Park et al. 1995). When the liposome has been internalized into the cell the enclosed substance can either diffuse through the liposome and endosome membranes into the cytoplasm or, in some cases, be released after lysozymal degradation of the carrier liposome. However, the problem of directing drugs to the nucleus of specific target cells still has to be solved.

SUMMARY OF THE INVENTION

The present invention solves the problem of directing drugs to the nucleus of specific target cells. By providing a new two-step targeting system for drug delivery, the invention provides for efficient delivery of different drugs to the nuclei of tumour cells. This means that the toxicity for normal organs is minimized. A further advantage is that the invention enables administration of therapeutic doses also to spread tumour cells and metastases. The purpose of the invention, is to treat or analyse both large tumour masses as well as small tumour cell clusters and single spread tumour cells.

According to the invention, large amounts of nuclides are delivered to the tumour cells and these nuclides will reach and bind to the nuclear DNA. The latter means that each radioactive decay will damage nuclear DNA and thereby the therapeutical process will be more efficient. In fact, the same amount of radioactive nuclides will impose at least ten times higher damage when the radioactivity is localised in the nuclear DNA than when localised outside the cell nucleus. The same arguments are valid when stable nuclides for neutron or photon activation are applied. The former characteristic of the invention, i.e. the delivery of large amounts of nuclides to the tumour cells, may for radioactive nuclides mean the difference between palliative and curative treatment. If conventional targeting processes with one step targeting are applied only palliative treatments appear possible.

Thus, in a first aspect the invention relates to a drug delivery system with two-step targeting, which comprises a combination of:

a) a lipid carrier provided with cell targeting agent(s) to target the drug delivery system to specific cells or tissue; and b) drug(s) enclosed in said lipid carrier and provided with a DNA targeting agent to target the drug to the nuclei of specific target cells.

The ratio between a) and b) may vary between 1 to $10^{-8}$, depending on the selected drug. The possibility of enclosing a high number of drugs in a lipid carrier means that the therapeutical efficiency will increase dramatically compared to known tumour drugs.

Preferably, the drugs are nuclides which either can be radioactive or stable or other DNA damaging substances, such as PNA and DNA alkylating agents. The drugs can be used either for therapeutic or diagnostic purposes. For nuclides, the above ratio between a) and b) is preferably in the lower range. For other DNA damaging substances, a smaller drug amount will suffice.

The lipid carrier can be any lipid aggregate with ability to enclose a drug and the preferred lipid carrier is a liposome, but a cubosome, hexasome or micelle may be equally or more potent for certain applications.

The cell targeting agent associated with the liposomal surface is selected from the group consisting of natural or synthetic ligands, antibodies, antibody fragments or other biomolecules suitable for the purpose.

According to the invention, different types of toxic loads, such as nuclides, can be used. Nuclides such as $^{125}$I (Auger radiation) and $^{211}$At (α-particles) provide high local ionization density and damage DNA very efficiently. These short range radiators require a targeting part which enables internalizing of the liposomes.

Among stable nuclides, boron ($^{10}$B) and gadolinium ($^{157}$Gd) are preferred types of cancer agents. After administration of the liposomes, the tumour area is, in this case, irrradiated by neutrons. Hereby, not stable $^{11}$B is formed from $^{10}$B and it rapidly disintegrates and gives particle radiation in the form of He (α particles) and Li nuclei, which effectively will kill the targeted cell (Carlsson et al. 1994). Other reactions take place after 157Gd captures a neutron. Stable nuclides suitable for photon activation (e.g. iodine and bromine) can also be considered. As for substances with short range radiation, the stable nuclide containing substance is to be located in the nucleus and most preferably bind to the nuclear DNA of the tumour cell.

Long range β-radiators, such as $^{131}$I, can be used as a complement. Such nuclides provide therapeutic action is even if the radionuclide only binds to the cytoplasm or the membrane of the cell. These types of β-radiators can be used to obtain cross-fire radiation in larger cell groupings.

The DNA targeting substance coupled directly to the nuclides can be a DNA-intercalator and/or a compound that interacts electrostatically or reacts chemically with DNA.

In a second aspect, the invention relates to a method for cancer therapy, comprising administering to a subject in need thereof a therapeutically efficient amount of the drug delivery system according to the invention. If the drug delivery system comprises a nuclide to be activated, the method also comprises the further step of irradiating the cancer area.

Thus, the invention relates to stabilized liposomes with double targeting, SLT-particles, for transport of a toxic substance to the cell nucleus. By enclosing the toxic substance in SLT-particles the uptake in tumours will be markedly increased at the same time as the interaction of the substance with healthy organs and tissues can be minimized. An appropriately selected targeting ligand allows administration of a toxic substance in therapeutic doses also to spread tumour cells.

DETAILED DESCRIPTION OF THE INVENTION

The invention will now be described more closely in relation to the accompanying drawings and the example.

EXAMPLE

Figure 1:
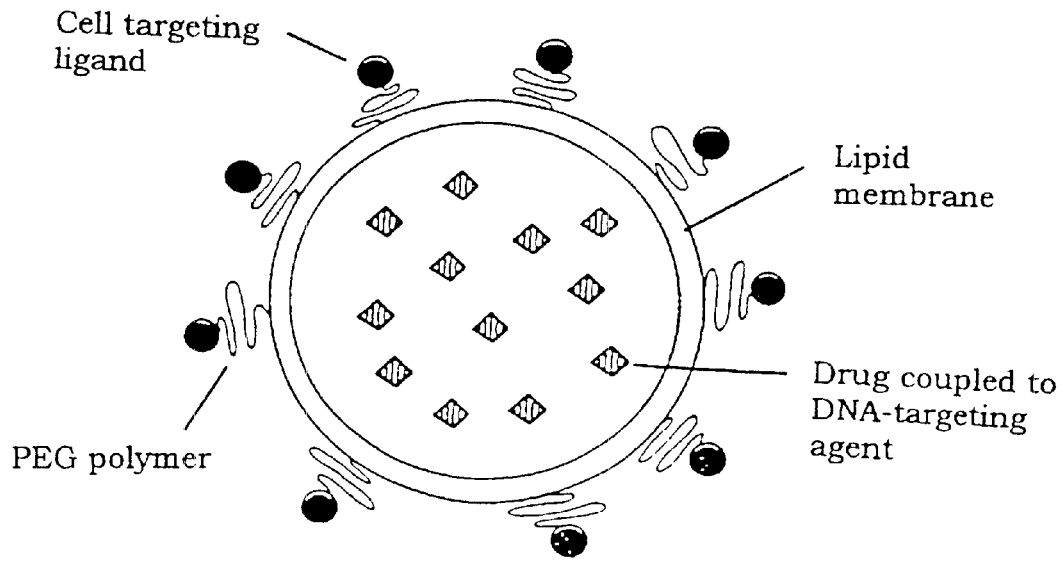
FIG. 1 shows an SLT-particle filled with a toxic substance.
Figure 2:
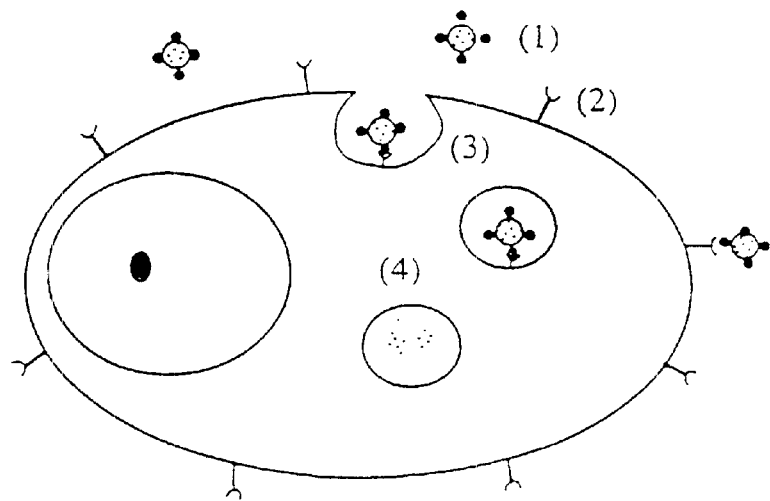
FIG. 2 shows SLT-particles (1) binding to receptors (2) on the surface of the target cell and being internalized by endocytosis (3). The toxic load is released (4) and can diffuse into the cytoplasm.

Preparation of SLT-particles with Different Properties a. The lipid carrier

The structure of the SLT-particles, their stability and leakage are mostly determined by the properties of the liposome part. The composition in the lipid membrane, as well as concentration and type of PEG-polymer, is adjusted according to the toxic load and the targeting agents which are used.

The size of the liposomes is adjusted to ensure optimum accumulation in the target tissue, target cells and/or target site. Cryo-transmission electromicroscopy, light scattering, NMR and different photophysical methods are used for the analyses of the liposome structure and size. A preferred size range of the liposomes is 50–150 nm.

Properly designed liposomes have the potential to carry large amounts of, in particular, water soluble substances. In order to optimize the amount of substance enclosed in the aqueous core of the liposome, the use of active loading techniques is often necessary. Effective loading techniques based on pH gradients are preferably used in the invention.

In summary, the lipid carrier must have the following properties:

- be stable against extracellular leakage of the entrapped drug
- have qualities which enables long circulation times
- be of a size that allows extravasation and accumulation in the tumour tissue.

b. First-step targeting agents

Coupling of targeting agents can be performed in a number of ways. Either the targeting agent can be provided with a lipophilic region, which is attached in the phospholipid membrane of the SLT particles, or they can be attached to the outer PEG-part by different chemical methods.

The cell targeting agents are preferably selected from the group of substances that bind to targets consisting of, for example, folate or EGF-receptors which are overexpressed in some types of tumour cancer cells; c-erb-B2 protein which is related to the EGF-receptor and often seems to be abundant in some adeno carcinomas, hematopoietic targets, such as the CD20 or CD32 antigens, which are expressed in some hematopoietic tumour diseases. Tumour specific mutations of receptors and tumour associated antigens, such as CEA, CA59, and CA19-9, are also candidate targets. Thus, several potential targets exist.

The cell targeting agent must have the following properties:

- high and specific affinity for receptors and antigens overexpressed on the target cells
- mediate intracellular deposition of toxic component
- show a stable coupling to the outside of the liposome.

c. Second-step targeting agents

Preferred compounds of the invention are stable nuclide- and radionuclide-carrying DNA-intercalators such as phenantridium, acridine and naphtalimide derivatives, and also compounds which intercalate electrostatically with DNA such as spermine, spermidine, and putrecine derivatives. The intercalators are especially suitable for tumour therapy because both the active substance and the DNA intercalation itself might provide a therapeutic action.

The second step targeting agent must have the following properties:

- high affinity for the nuclear DNA
- high water solubility at physiological pH and ionic strength
- permit efficient loading to fill the lipid carrier
- show minimal leakage when enclosed in the lipid carrier d. Drugs (nuclides)

Nuclides for Therapy

Short range radiators, which give high local ionization density, e.g. 125I (Auger radiation) and $^{211}At$ ((α-particles) will be applied to obtain maximum effect in a single targeted cell.

The stable nuclide $^{10}$B is another drug candidate according to the invention. $^{10}$B is activated by externally applied neutrons. $^{157}$Gd is another candidate for neutron activation. Other alternatives are stable iodine or bromine which can be activated with photons.

In addition, these can be combined with radionuclides with long range β-radiation, primarily halogens such as $^{131}$I, but also other nuclides such as $^{32}$P and the metals $^{67}$Cu, $^{90}$Y and $^{189}$Re. These are applied to obtain cross-fire radiation in bigger cell groupings.

Nuclides for Distribution Studies in Vivo

Gamma radiators will be incorporated in lipid carriers to allow distribution studies in humans by PET- and SPECT-techniques (Nilsson et al 1995, Westlin et al 1995). For this purpose we also intend to use positron radiators in the halogen group with relatively long half lives such as $^{76}$Br and 124I, which are suitable for "macromolecular" PET. For SPECT we intend to use halogens such as $^{131}$I. Different types of radioactive metals can also be applied.

e. Composition of one promising SLT-particle

Unilamellar liposomes with a diameter of 120 nm composed of 55 mol % 1,2-distearoyl-sn-glycero-3-phosphocholine (DSPC), 40 mol % cholesterol (Chol) and 5 mol % 1,2-distearoyl-sn-glycero-3-phosphoethanolamine-N-[poly(ethylene glycol)-2000] (PEG(2000)-DSPE) The liposomes are prepared by multiple extrusion through polycarbonate filters with pore size 100 nm.

Enclosed in the aqueous interior of the liposomes is the compound 1,8-diamino-4-N-3- [12-(N-9-acridinyl-3-aminopropyl)-p-carborane-1-yl] propyl-4-azooctane hydrogen chloride (WSA1) having the following structural formula:

References

Carlsson, J.; Gedda, L.; Grönvik, C.; Hartman, T.; Lindström, A.; Lindström; P.; Lundquist, H.; Lövquist, A.; Malmquist, J.; Olsson, P.; Essand, M.; Pontén, J.; Sjöberg, S.; and Westermark, B. 1994. Strategy for boron neutron capture therapy against tumor cells with over-expression of the epidermal growth factor-receptor. Int. J. Radiation Oncol. Biol. Phys. 30:105–115.

Gedda, L.; Silvander, M.; Sjöberg, S.; Tjarks, W., and Carlsson, J. 1997. Cytotoxicity and subcellular localization of boronated phenantridinium analogues. Anti-Cancer Drug Design 12:671–85.

Kirpotin, D.; Park, J. W.; Hong, K.; Zalipsky, S.; Li, W.; Carter, P.; Benz, C. C., and Papahadjopoulos, D. 1997. Sterically stabilized anti-HER2 immunoliposomes: design and targeting to human breast cancer cells in vitro. Biochemistry 36:66–75.

Lasic, D. and Martin, F. (Eds.), 1995. Stealth Liposomes. CRC Press, Boca Raton.

Lee, R. J. and Low, P. S. 1994. Delivery of liposomes into cultured KB cells via folate-receptor mediated endocytosis. J. Biol. Chem. 4:3198–3204.

Nilsson, S.; Reubi, J. C.; Kälkner, K. M.; Laissue, J. A.; Horisberger, U.; Olerud, C., and Westlin, J. E. 1995. Metastatic hormone-refractory prostatic adenocarcinoma express somostatin receptors and is visualized by 11-In-DTPA-D-Phe-1-octreotide scintigraphy. Cancer Res. 55:5805–5810.

Park, J. W., Hong, K., Carter, P., Asgari, H., Guo, L. Y., Keller, G. A., Wirth, C., Shalaby, R., Kotts, C., Wood, W. I., Papahadjopoulos, D., and Benz, C. C. 1995. Development of anti-p185HER2 immunoliposomes for cancer therapy. Proc. Natl. Acad. Sci. U.S.A. 92, 1327–1331.

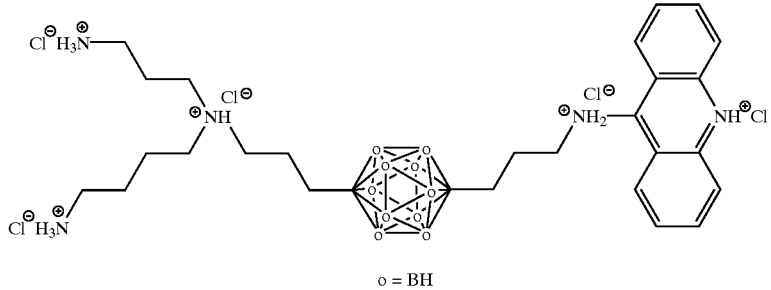

o = BH

The liposomes are loaded by use of citric acid pH-gradient. Liposomes are prepared in 500 mM citrate buffer with pH 4.0 The external medium is titrated to pH 7.7 with sodium carbonate. WSA is thereafter added and allowed to load for 20 minutes at 60° C. The final formulation contains 40 mg/ml of total lipid and 12 mg/ml of WSA1 which corresponds to about 1×10$^5$ WSA, or 1×10$^6$ $^{10}$B, per liposome. The formulation is stable in both buffer and serum, less than 15% of the encapsulated WSA 1 is released after 48h incubation at 37° C.

The liposomes have epidermal growth factor (EGF), for targeting against the normal EGF receptor, or a ligand directed against mutated EGF receptor covalently linked to the distal end of the PEG chains. Alternatively, PEG is excluded in the liposome preparation and the ligand is coupled directly to the liposome surface via conjugation to DSPE.

Press, O. W. 1995. Treatment of recurrent lymphomas with unmodified antibodies and radioimmunoconjugates. Tumor Targeting 1:31–35.

Sjöberg, S.; Carlsson, J.; Ghaneolhusseini, H.; Gedda, L.; Hartman, T; Malmquist, J.; Naeslund, C.; Olsson, P.; and Tjarks, W. "Chemistry and biology of some low molecular weight boron compounds for Boron Neutron Capture Therapy", J. Neuro-Oncol. 1997, 33, 41–52.

Sjöberg, S. "Boron Chemistry for NCT".."In; Larsson, B.; Crawford, J. and Weinreich (eds.) Advances in NCT Vol. 2: Chemistry and Biology. Elsevier Scientific, Amsterdam 1997, pp 3–21.

Westlin, J. E.; Edgren, M.; Letocha, H.; Stridsberg, M.; Wilander, E., and Nilsson, S. Positron emission tomography utilizing 11-C-5-hyrdroxytryphtophan, plasma biochemistry and neuroendocrine immunohistochemistry of metastatic renal cell carcinoma. Oncology Reports 2:543–548.

Ghaneolhosseini H., Tjarks W., and Sjöberg S. Synthesis of Boronated Phenanthridinium Derivatives for potential Use in Boron Neutron Capture Therapy (BNCT). *Tetrahedron* 1997, 53, 17519–17526.

What is claimed is:

1. A drug deliver), system with two-step targeting comprising:
   a) a lipid carrier provided with cell targeting agent(s) to target the drug delivery system to specific cells or tissue; and
   b) drug(s) enclosed in said lipid carrier and provided with a DNA targeting agent to target the drug to the nucleus of target tumor cells, wherein the drugs are radioactive nuclides or stable nuclides suitable for activation,
   wherein the ratio between a) and b) is between 1 and $10^{-8}$.

2. A drug delivery system according to claim 1, wherein the cell targeting agent is selected from the group consisting of ligands, antibodies and antibody fragments.

3. A drug delivery system according to claim 1, wherein the DNA targeting agent is a DNA intercalator or an agent that interacts electrostatically or reacts chemically with DNA.

4. A drug delivery system according to claim 1, comprising:
   a) as the lipid carrier, unilamellar liposomes with a diameter of 120 nm composed of 55 mol %, 1,2-distearoyl-sn-glycero-3-phosphocholine (DSPC), 40 mol % cholesterol (Chol) and 5 mol % 1,2-distearoyl-sn-glycero-3-phosphoethanolamine-N-(poly(ethylene glycol)-2000) (PEG(2000)-DSPE); and as the cell targeting agent, epidermal growth factor (EGF), or a substance binding to tumor specific, mutated EGF receptor, covalently linked to the distal end of the PEG chains; and
   b) as the DNA targeted drug, the compound 1,8-diamino-4-N-3-(12-(N-9-acridinyl-3-aminopropyl)-p-carborane-1-yl) propyl-4-azooctane hydrogen chloride (WSA1).

5. A method for cancer therapy, comprising administering to a subject in need thereof a therapeutically efficient amount of the drug delivery system according to claim 1 in which the drugs are nuclides suitable for activation, and subsequently irradiating the cancer area.

6. A method for cancer therapy and/or diagnostics, comprising administering to a subject in need thereof a therapeutically and/or diagnostically efficient amount of the drug delivery system according to claim 1 in which the drugs are radioactive.

7. A drug delivery system according to claim 2, wherein the DNA targeting agent is a DNA intercalator or an agent that interacts electrostatically or reacts chemically with DNA.

8. A drug delivery system according to claim 2, comprising:
   a) as the lipid carrier, unilamellar liposomes with a diameter of 120 nm composed of 55 mol %, 1,2-distearoyl-sn-glycero-3-phosphocholine (DSPC), 40 mol % cholesterol (Chol) and 5 mol % 1,2-distearoyl-sn-glycero-3-phosphoethanolamine-N-(poly(ethylene glycol)-2000) (PEG(2000)-DSPE); and as the cell targeting agent, epidermal growth factor (EGF), or a substance binding to tumor specific, mutated EGF receptor, covalently linked to the distal end of the PEG chains; and
   b) as the DNA targeted drug, the compound 1,8-diamino-4-N-3-(12-(N-9-acridinyl-3-aminopropyl)-p-carborane-1-yl) propyl-4-azooctane hydrogen chloride (WSA1).

9. A drug delivery system according to claim 3, comprising:
   a) as the lipid carrier, unilamellar liposomes with a diameter of 120 nm composed of 55 mol %, 1,2-distearoyl-sn-glycero-3-phosphocholine (DSPC), 40 mol % cholesterol (Chol) and 5 mol % 1,2-distearoyl-sn-glycero-3-phosphoethanolamine-N-(poly(ethylene glycol)-2000) (PEG(2000)-DSPE); and as the cell targeting agent, epidermal growth factor (EGF), or a substance binding to tumor specific, mutated EGF receptor, covalently linked to the distal end of the PEG chains; and
   b) as the DNA targeted drug, the compound 1,8-diamino-4-N-3-(12-(N-9-acridinyl-3-aminopropyl)-p-carborane-1-yl) propyl-4-azooctane hydrogen chloride (WSA1).

10. A drug delivery system according to claim 1, wherein the cell targeting agent comprises epidermal growth factor (EGF), or a substance binding to tumor specific, mutated EGF receptor.

11. A drug delivery system according to claim 1, wherein the DNA targeting agent comprises a derivative of phenantridium, acridine, naphthalimide, spermine, spermidine, or putrecine.

12. A drug delivery system according to claim 1, wherein the DNA targeted drug comprises 1,8-diamino-4-N-3-(12-(N-9-acridinyl-3-aminopropyl)-p-carborane-1-yl) propyl-4-azooctane hydrogen chloride (WSA1).

13. A method for cancer therapy, comprising administering to a subject in need thereof a therapeutically efficient amount of the drug delivery system according to claim 4, and subsequently irradiating the cancer area.

14. A method for cancer therapy, comprising administering to a subject in need thereof a therapeutically efficient amount of the drug delivery system according to claim 10 in which the drugs are nuclides suitable for activation, and subsequently irradiating the cancer area.

15. A method for cancer therapy, comprising administering to a subject in need thereof a therapeutically efficient amount of the drug delivery system according to claim 11 in which the drugs are nuclides suitable for activation, and subsequently irradiating the cancer area.

16. A method for cancer therapy comprising administering to a subject in need thereof a therapeutically efficient amount of the drug delivery system according to claim 12 and subsequently irradiating the cancer area.

* * * * *

UNITED STATES PATENT AND TRADEMARK OFFICE
CERTIFICATE OF CORRECTION

PATENT NO. : 6,562,316 B1
DATED : May 13, 2003
INVENTOR(S) : Katarina Edwards et al.

It is certified that error appears in the above-identified patent and that said Letters Patent is hereby corrected as shown below:

<u>Column 7,</u>
Line 4, change "deliver)," to -- delivery --

Signed and Sealed this

Twenty-second Day of July, 2003

JAMES E. ROGAN
*Director of the United States Patent and Trademark Office*